(12) United States Patent
Schubert et al.

(10) Patent No.: US 7,847,115 B2
(45) Date of Patent: Dec. 7, 2010

(54) PROCESS FOR PREPARING POROUS ORGANIC FRAMEWORK MATERIALS

(75) Inventors: Markus Schubert, Ludwigshafen (DE); Ulrich Mueller, Neustadt (DE); Hendrick Mattenheimer, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 271 days.

(21) Appl. No.: 12/161,024

(22) PCT Filed: Feb. 8, 2007

(86) PCT No.: PCT/EP2007/051211
§ 371 (c)(1), (2), (4) Date: Jul. 16, 2008

(87) PCT Pub. No.: WO2007/090864
PCT Pub. Date: Aug. 16, 2007

(65) Prior Publication Data
US 2010/0160661 A1  Jun. 24, 2010

(51) Int. Cl.
C07F 3/00 (2006.01)
C07F 15/00 (2006.01)
C07F 5/02 (2006.01)

(52) U.S. Cl. ............... 556/132; 556/115; 556/147; 568/3; 568/6

(58) Field of Classification Search .............. 556/115, 556/132, 147; 568/3, 6
See application file for complete search history.

(56) References Cited

U.S. PATENT DOCUMENTS 5,648,508 A   7/1997   Yaghi

FOREIGN PATENT DOCUMENTS

DE  101 11 230    9/2002
EP  0 790 253     8/1997
WO  02 070526    9/2002
WO  02 088148   11/2002
WO  03 102000   12/2003

OTHER PUBLICATIONS

U.S. Appl. No. 12/668,436, filed Jan. 11, 2010, Schubert, et al.
U.S. Appl. No. 12/594,604, filed Oct. 5, 2009, Stein, et al.
U.S. Appl. No. 12/597,616, filed Oct. 26, 2009, Schubert, et al.
U.S. Appl. No. 12/601,022, filed Nov. 20, 2009, Schubert, et al.
U.S. Appl. No. 12/600,539, filed Nov. 17, 2009, Schubert, et al.
O'Keeffe, M. et al., "Frameworks for Extended Solids: Geometrical Design Principles", Journal of Solid State Chemistry, vol. 152, pp. 3-20, (2000).
Eddaoudi, Mohamed et al., "Design and synthesis of metal-carboxylate frameworks with permanent microporosity", Topics in Catalysis, vol. 9, pp. 105-111, (1999).
Sudik, Andrea C. et al., "Design, Synthesis, Structure, and Gas (N2, Ar, CO2, CH4, and H2) Sorption Properties of Porous Metal-organic Tetrahedral and Heterocuboidal Polyhedra", J. Am. Chem. Soc., vol. 127, pp. 7110-7118, (2005).
Rowsell, Jesse L. C. et al., "Hydrogen Sorption in Functionalized Metal-Organic Frameworks", J. Am. Chem. Soc., vol. 126, pp. 5666-5667, (2004).
Li, Haillan et al., "Design and synthesis of an exceptionally stable and highly porous metal-organic framework", Nature, vol. 402, pp. 276-279, (1999).
Chen, Banglin et al., "Interwoven Metal-Organic Framework on a Periodic Minimal Surface with Extra-Large Pores", Science, vol. 291, pp. 936-937 and 1021-1023, (2001).
Cote, Adrien P. et al., "Porous, Crystalline, Covalent Organic Frameworks", Science, vol. 310, pp. 1116-1170, (2005).

*Primary Examiner*—Porfirio Nazario Gonzalez
(74) *Attorney, Agent, or Firm*—Oblon, Spivak, McClelland, Maier & Neustadt, L.L.P.

(57) ABSTRACT

The present invention relates to a process for preparing porous organic frameworks by reaction of a reaction mixture in a liquid phase comprising the appropriate starting compounds in the presence of a nonaqueous organic solvent in the presence of and/or with liberation of water, wherein the latter is withdrawn from the liquid phase of the reaction mixture during the reaction. Here, frameworks having relatively high specific surface areas can be obtained in a reproducible way.

10 Claims, No Drawings

PROCESS FOR PREPARING POROUS ORGANIC FRAMEWORK MATERIALS

The present invention relates to a process for preparing porous organic frameworks.

Porous organic frameworks form an interesting class of substances which can provide an alternative to inorganic zeolites for a wide variety of applications.

Such applications are, for example, in the field of the storage, removal or controlled release of chemical substances, for example gases, or in the field of catalysis. Here, the porosity of the organic material plays a particularly critical role. As a result of the pores present in defined form in the organic framework, the specific surface area of the material is increased and, in addition, selective separation of mixtures is made possible. The same applied to such materials when they are used as support material in chemical reactions, for example in catalytic reactions.

A specific group of these porous organic frameworks is formed by metal organic frameworks. These are known in the prior art and typically comprise at least one at least bidentate organic compound coordinated to a metal ion. Such metal organic frameworks (MOFs) are described, for example, in U.S. Pat. No. 5,648,508, EP-A 0 790 253, M. O. Keeffe, J. Sol. State Chem., 152 (2000), 3-20; H. Li et al., Nature 402 (1999), 276; M. Eddaoudi, Topics in catalysis 9 (1999), 105-111; B. Chen et al., Science 291 (2001), 1021-1023 and DE-A 101 11 230.

As a specific group of these metal organic frameworks, the most recent literature has described "limited" frameworks in which, as a result of specific choice of the organic compound, the framework does not extend infinitely but with formation of polyhedra. A. G. Sudik, et al., J. Am. Chem. Soc. 127 (2005), 7110-7118, describe such special frameworks. Here, these are referred to as metal organic polyhedra (MOPs) to distinguish them.

A further modification of such porous organic frameworks is the covalent organic frameworks (COFs). These are frameworks in which the central metal atom of the metal organic frameworks is replaced by an organic boron compound which preferably has at least two boronic groups (R—B(OH)$_2$, where R is an organic radical). A. P. Cote, et al. Science 310 (2005), 1116-1170, describe, for example, such frameworks.

All of these organic frameworks are porous. The specific surface area of such materials, which strongly influences their properties, is closely related to the porosity. The specific surface area determined by the Langmuir method may be regarded as a measure for characterizing such surface areas.

In the preparation of such materials, it is not only a good yield but also the production of high specific surface areas and the reproducibility in the preparation which are of great importance. This applies particularly in the preparation of large amounts of framework.

Numerous methods of synthesizing, for example, metal organic frameworks such as MOF-5 (IRMOF-1) are described in the literature.

Thus, for example, H. Li, et al., Nature 402 (1999), 276-279, describes the synthesis of MOF-5, with a Langmuir surface area of about 2900 m$^2$/g being able to be achieved.

In WO-A 02/070526, for example, specific solvents are used to prepare MOF-5. A specific surface area of 1063 m$^2$/g was obtained here.

In WO-A 02/088148, too, various methods of preparing IRMOF-1 (MOF-5) are disclosed.

The preparation of MOF-5, in which a particularly high surface area was able to be achieved, is described in WO-A 03/102000 and by J. L. C. Rowsell, et al., J. Am. Chem. Soc. 126 (2004), 5666-5667.

All these references show that despite the same reaction procedures in principle, porous organic frameworks which can have very different specific surface areas and thus different properties are obtained.

There is therefore a need to provide a method of preparation which, particularly in the preparation of relatively large amounts of porous organic frameworks, avoids the above-described disadvantages.

It is thus an object of the present invention to provide a process for preparing porous organic frameworks, which produces sufficiently large amounts of such frameworks with the frameworks having a very high specific surface area and being able to be prepared with high reproducibility.

The object is achieved by a process for preparing a porous metal organic, if appropriate limited, framework, which comprises the step:

reaction of a reaction mixture in a liquid phase comprising at least one metal compound with at least one at least bidentate organic compound which can be coordinated to the metal, in the presence of a nonaqueous organic solvent in the presence of and/or with liberation of water, with the organic compound having at least two atoms selected independently from the group consisting of oxygen, sulfur and nitrogen via which the organic compound can coordinate to the metal, wherein water is withdrawn from the liquid phase of the reaction mixture during the reaction.

The object is additionally achieved by a process for preparing a porous organoboron, if appropriate limited, framework, which comprises the step:

reaction of a reaction mixture in a liquid phase comprising at least one compound having at least two boronic groups with at least one at least bifunctional organic compound which can be covalently bound to a boronic group, in the presence of a nonaqueous organic solvent, with the at least bifunctional organic compound having at least two atoms selected independently from the group consisting of oxygen, sulfur and nitrogen via which the bifunctional organic compound can be covalently bound to a boronic group, wherein water is withdrawn from the liquid phase of the reaction mixture during the reaction.

It has surprisingly been found that the above-described porous organic frameworks (MOFs, MOPs, COFs) having comparatively high specific surface areas and readily reproducible properties which have a lower standard deviation than in the prior art can be produced by withdrawing water from the reaction mixture during the formation of the porous organic frameworks.

In the case of metal organic frameworks, this water can be present in the form of water of crystallization of the metal compound in the reaction mixture. After reaction of the metal compound, the no longer coordinated water of crystallization is present in the reaction mixture and can be withdrawn therefrom. It is also possible for organic solvents which are not fully water-free to be used. Here too, the water present in the reaction mixture as a result can be withdrawn therefrom. Finally, water can also be formed in the reaction itself. This applies, for example, when the metal compound is present in the form of a metal hydroxide or a metal oxide in the reaction mixture and reaction with the at least bidentate organic compound, which can be, for example, an organic carboxylic acid, occurs. Here, water is liberated as a result of the formation of the metal complex. The metal compound does not have to be added to the reaction mixture as hydroxide or oxide. Rather, it can also be present in the form of a metal salt and the hydroxide ions necessary for formation of the water can be generated by addition of a base such as sodium hydroxide or by means of the solvent.

In the case of the organoboron frameworks, water is, in particular, generated by the boronic acid being reacted with, for example, an alcohol.

The removal of the water from the reaction mixture can be effected, in particular, by distillation, by stripping or by means of adsorbents. Suitable adsorbents are, for example, aluminum oxide, silica gel or a molecular sieve, in particular 3 Å or 4 Å molecular sieve.

In the case of stripping, constituents of a liquid phase are removed from this liquid phase by passing gases through it and transferred into a gas phase.

It is advantageous, inter alia, for the reaction to be able to take place with stirring, which is also advantageous in the case of scale-up. In this way, it is possible to obtain larger amounts of the desired porous organic framework per reaction.

The reaction is preferably carried out at a pressure of not more than 2 bar (absolute). However, the pressure is more preferably not more than 1200 mbar (absolute). The reaction particularly preferably takes place at atmospheric pressure.

The reaction can be carried out at room temperature or elevated temperature. However, the reaction is preferably carried out at a reaction temperature in the range from 80° C. to 180° C. Greater preference is given to a reaction temperature of from 100° C. to 150° C.

The metal compound can, as mentioned above, be a metal salt. Examples of such salts are nitrates, sulfates, chlorides, fluorides, iodides, hydroxides, oxides and alkoxylates. Depending on the metal used, such compounds may also be present as hydrates. An example which may be mentioned is zinc nitrate which is commercially available both as tetrahydrate and as hexahydrate.

The metal organic frameworks according to the present invention comprise pores, in particular micropores and/or mesopores. Micropores are defined as pores having a diameter of 2 nm or less and mesopores are defined by a diameter in the range from 2 to 50 nm, in each case in accordance with the definition given in Pure & Applied Chem. 57 (1985), 603-619, in particular on page 606. The presence of micropores and/or mesopores can be checked by means of sorption measurements which determine the uptake capacity of the MOF for nitrogen at 77 kelvin in accordance with DIN 66131 and/or DIN 66134.

The specific surface area, calculated according to the Langmuir model in accordance with DIN 66135 (DIN 66131, 66134), of an MOF in powder form is preferably greater than 5 m$^2$/g, more preferably greater than 10 m$^2$/g, more preferably greater than 50 m$^2$/g, even more preferably greater than 500 m$^2$/g, even more preferably greater than 1000 m$^2$/g and particularly preferably greater than 1500 m$^2$/g.

Shaped MOF bodies can have a lower specific surface area; but it is preferably greater than 10 m$^2$/g, more preferably greater than 50 m$^2$/g, even more preferably greater than 500 m$^2$/g.

The metal component in the framework is preferably selected from among groups Ia, IIa, IIIa, IVa to VIIIa and Ib to VIb. Particular preference is given to Mg, Ca, Sr, Ba, Sc, Y, Ti, Zr, Hf, V, Nb, Ta, Cr, Mo, W, Mn, Re, Fe, Ro, Os, Co, Rh, Ir, Ni, Pd, Pt, Cu, Ag, Au, Zn, Cd, Hg, B, Al, Ga, In, Tl, Si, Ge, Sn, Pb, As, Sb and Bi. Greater preference is given to Zn, Al, Mg, Ca, Cu, Ni, Fe, Pd, Pt, Ru, Rh, Co, Zr and Ti. Particular preference is given to Zn, Al, Ni, Cu, Mg, Ca, Fe. With regard to ions of these elements, particular mention may be made of $Mg^{2+}$, $Ca^{2+}$, $Sr^{2+}$, $Ba^{2+}$, $Sc^{3+}$, $Y^{3+}$, $Tr^+$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2+}$, $Ni^+$, $Pd^{2+}$, $Pd^+$, $Pt^{2+}$, $Pr$, $Cu^{2+}$, $Cu^+$, $Ag^+$, $Au^+$, $Zn^{2+}$, $Cd^{2+}$, $Hg^{2+}$, $Al^{3+}$, $Ga^{3+}$, $In^{3+}$, $Tl^{3+}$, $Sr^+$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$ and $Bi^+$.

The at least one at least bidentate organic compound has at least two atoms which are selected independently from the group consisting of oxygen, sulfur and nitrogen via which the organic compound can coordinate to the metal. These atoms can be part of the skeleton of the organic compound or be functional groups.

As functional groups via which the abovementioned coordinate bonds can be formed, mention may be made by way of example of, in particular: OH, SH, NH$_2$, NH(—R—H), N(R—H)$_2$, CH$_2$OH, CH$_2$SH, CH$_2$NH$_2$, CH$_2$NH(—R—H), CH$_2$N(—R—H)$_2$, —CO$_2$H, COSH, —CS$_2$H, —NO$_2$, —B(OH)$_2$, —SO$_3$H, —Si(OH)$_3$, —Ge(OH)$_3$, —Sn(OH)$_3$, —Si(SH)$_4$, —Ge(SH)$_4$, —Sn(SH)$_3$, —PO$_3$H$_2$, —AsO$_3$H, —AsO$_4$H, —P(SH)$_3$, —As(SH)$_3$, —CH(RSH)$_2$, —C(RSH)$_3$, —CH(RNH$_2$)$_2$, —C(RNH$_2$)$_3$, —CH(ROH)$_2$, —C(ROH)$_3$—CH(RCN)$_2$, —C(RCN)$_3$, where R is preferably, for example, an alkylene group having 1, 2, 3, 4 or 5 carbon atoms, for example a methylene, ethylene, n-propylene, isopropylene, n-butylene, isobutylene, tert-butylene or n-pentylene group, or an aryl group comprising 1 or 2 aromatic rings, for example 2 C$_6$ rings, which may, if appropriate, be fused and may, independently of one another, be appropriately substituted by in each case at least one substituent and/or may, independently of one another, comprise in each case at least one heteroatom, for example N, O and/or S. In likewise preferred embodiments, mention may be made of functional groups in which the abovementioned radical R is not present. In this regard, mention may be made of, inter alia, —CH(SH)$_2$, —C(SH)$_3$, —CH(NH$_2$)$_2$, CH(NH(R—H))$_2$, CH(N(R—H)$_2$)$_2$, C(NH(R—H))$_3$, C(N(R—H)$_2$)$_3$, —C(NH$_2$)$_3$, —CH(OH)$_2$, —C(OH)$_3$, —CH(CN)$_2$, —C(CN)$_3$.

The at least two functional groups can in principle be bound to any suitable organic compound as long as it is ensured that the organic compound comprising these functional groups is capable of forming the coordinate bond and of producing the framework.

The organic compounds which comprise the at least two functional groups are preferably derived from a saturated or unsaturated aliphatic compound or an aromatic compound or a both aliphatic and aromatic compound.

The aliphatic compound or the aliphatic part of the both aliphatic and aromatic compound can be linear and/or branched and/or cyclic, with a plurality of rings per compound also being possible. The aliphatic compound or the aliphatic part of the both aliphatic and aromatic compound more preferably comprises from 1 to 18, more preferably from 1 to 14, more preferably from 1 to 13, more preferably from 1 to 12, more preferably from 1 to 11 and particularly preferably from 1 to 10, carbon atoms, for example 1, 2, 3, 4, 5, 6, 7, 8, 9 or 10 carbon atoms. Particular preference is here given to, inter alia, methane, adamantane, acetylene, ethylene or butadiene.

The aromatic compound or the aromatic part of the both aromatic and aliphatic compound can have one or more rings, for example two, three, four or five rings, with the rings being able to be present separately from one another and/or at least two rings being able to be present in fused form. The aromatic compound or the aromatic part of the both aliphatic and aromatic compound particularly preferably has one, two or three rings, with particular preference being given to one or two rings. Furthermore, each ring of said compound can comprise, independently of one another, at least one heteroatom such as N, O, S, B, P, Si, preferably N, O and/or S. More preferably, the aromatic compound or the aromatic part of the both aromatic and aliphatic compound comprises one or two $C_6$ rings; in the case of two rings, they can be present either separately from one another or in fused form. Aromatic compounds of which particular mention may be made are benzene, naphthalene and/or biphenyl and/or bipyridyl and/or pyridyl.

The at least bidentate organic compound is particularly preferably derived from a dicarboxylic, tricarboxylic or tetracarboxylic acid or a sulfur analogue thereof. Sulfur analogues are the functional groups —C(=O)SH and its tautomer and C(=S)SH, which can be used in place of one or more carboxylic acid groups.

For the purposes of the present invention, the term "derived" means that the at least bidentate organic compound can be present in partly deprotonated or completely deprotonated form in the framework. Furthermore, the at least bidentate organic compound can comprise further substituents such as —OH, —NH₂, —OCH₃, —CH₃, —NH(CH₃), —N(CH₃)₂, —CN and halides.

The at least bidentate organic compound is more preferably an aliphatic or aromatic acyclic or cyclic hydrocarbon which has from 1 to 18 carbon atoms and, in addition, has exclusively at least two carboxy groups as functional groups.

For the purposes of the present invention, mention may be made by way of example of dicarboxylic acids such as oxalic acid, succinic acid, tartaric acid, 1,4-butanedicarboxylic acid, 1,4-butenedicarboxylic acid, 4-oxopyran-2,6-dicarboxylic acid, 1,6-hexanedicarboxylic acid, decanedicarboxylic acid, 1,8-heptadecanedicarboxylic acid, 1,9-heptadecanedicarboxylic acid, heptadecanedicarboxylic acid, acetylenedicarboxylic acid, 1,2-benzenedicarboxylic acid, 1,3-benzenedicarboxylic acid, 2,3-pyridinedicarboxylic acid, pyridine-2,3-dicarboxylic acid, 1,3-butadiene-1,4-dicarboxylic acid, 1,4-benzene-dicarboxylic acid, p-benzenedicarboxylic acid, imidazole-2,4-dicarboxyolic acid, 2-methylquinoline-3,4-dicarboxylic acid, quinoline-2,4-dicarboxylic acid, quinoxaline-2,3-dicarboxylic acid, 6-chloroquinoxaline-2,3-dicarboxylic acid, 4,4'-diamino-phenylmethane-3,3'-dicarboxylic acid, quinoline-3,4-dicarboxylic acid, 7-chloro-4-hydroxyquinoline-2,8-dicarboxylic acid, diimidedicarboxylic acid, pyridine-2,6-dicarboxylic acid, 2-methylimidazole-4,5-dicarboxylic acid, thiophene-3,4-dicarboxylic acid, 2-isopropylimidazole-4,5-dicarboxylic acid, tetrahydropyran-4,4-dicarboxylic acid, perylene-3,9-dicarboxylic acid, perylenedicarboxylic acid, Pluriol E 200-dicarboxylic acid, 3,6-dioxaoctanedicarboxylic acid, 3,5-cyclohexadiene-1,2-dicarboxylic acid, octadicarboxylic acid, pentane-3,3-dicarboxylic acid, 4,4'-diamino-1,1'-biphenyl-3,3'-dicarboxylic acid, 4,4'-diaminobiphenyl-3,3'-dicarboxylic acid, benzidine-3,3'-dicarboxylic acid, 1,4-bis(phenylamino)benzene-2,5-dicarboxylic acid, 1,1'-binaphthyldicarboxylic acid, 7-chloro-8-methylquinoline-2,3-dicarboxylic acid, 1-anilinoanthraquinone-2,4'-dicarboxylic acid, polytetrahydrofuran-250-dicarboxylic acid, 1,4-bis(carboxymethyl)piperazine-2,3-dicarboxylic acid, 7-chloroquinoline-3,8-dicarboxylic acid, 1-(4-carboxy)phenyl-3-(4-chloro)phenylpyrazoline-4,5-dicarboxylic acid, 1,4,5,6,7,7-hexachloro-5-norbornene-2,3-dicarboxylic acid, phenylindanedicarboxylic acid, 1,3-dibenzyl-2-oxoimidazolidine-4,5-dicarboxylic acid, 1,4-cyclohexanedicarboxylic acid, naphthalene-1,8-dicarboxylic acid, 2-benzoyl-benzene-1,3-dicarboxylic acid, 1,3-dibenzyl-2-oxoimidazolidine-4,5-cis-dicarboxylic acid, 2,2'-biquinoline-4,4'-dicarboxylic acid, pyridine-3,4-dicarboxylic acid, 3,6,9-trioxaundecanedicarboxylic acid, hydroxybenzophenonedicarboxylic acid, Pluriol E 300-dicarboxylic acid, Pluriol E 400-dicarboxylic acid, Pluriol E 600-dicarboxylic acid, pyrazole-3,4-dicarboxylic acid, 2,3-pyrazinedicarboxylic acid, 5,6-dimethyl-2,3-pyrazinedicarboxylic acid, (bis(4-aminophenyl)ether)diimide-dicarboxylic acid, 4,4'-diaminodiphenylmethanediimidedicarboxylic acid, (bis(4-amino-phenyl)sulfone)diimidedicarboxylic acid, 1,4-naphthalenedicarboxylic acid, 2,6-naphthalenedicarboxylic acid, 1,3-adamantanedicarboxylic acid, 1,8-naphthalene-dicarboxylic acid, 2,3-naphthalenedicarboxylic acid, 8-methoxy-2,3-naphthalene-dicarboxylic acid, 8-nitro-2,3-naphthalenecarboxylic acid, 8-sulfo-2,3-naphthalene-dicarboxylic acid, anthracene-2,3-dicarboxylic acid, 2',3'-diphenyl-p-terphenyl-4,4''-dicarboxylic acid, (diphenyl ether)-4,4'-dicarboxylic acid, imidazole-4,5-dicarboxylic acid, 4(1H)-oxothiochromene-2,8-dicarboxylic acid, 5-tert-butyl-1,3-benzenedicarboxylic acid, 7,8-quinolinedicarboxylic acid, 4,5-imidazoledicarboxylic acid, 4-cyclohexene-1,2-dicarboxylic acid, hexatriacontanedicarboxylic acid, tetradecanedicarboxylic acid, 1,7-heptadicarboxylic acid, 5-hydroxy-1,3-benzenedicarboxylic acid, 2,5-dihydroxy-1,4-dicarboxylic acid, pyrazine-2,3-dicarboxylic acid, furan-2,5-dicarboxylic acid, 1-nonene-6,9-dicarboxylic acid, eicosenedicarboxylic acid, 4,4'-dihydroxydiphenylmethane-3,3'-dicarboxylic acid, 1-amino-4-methyl-9,10-dioxo-9,10-dihydroanthracene-2,3-dicarboxylic acid, 2,5-pyridinedicarboxylic acid, cyclohexene-2,3-dicarboxylic acid, 2,9-dichlorofluorubin-4,11-dicarboxylic acid, 7-chloro-3-methylquinoline-6,8-dicarboxylic acid, 2,4-dichlorobenzophenone-2',5'-dicarboxylic acid, 1,3-benzenedicarboxylic acid, 2,6-pyridinedicarboxylic acid, 1-methylpyrrole-3,4-dicarboxylic acid, 1-benzyl-1H-pyrrole-3,4-dicarboxylic acid, anthraquinone-1,5-dicarboxylic acid, 3,5-pyrazoledicarboxylic acid, 2-nitrobenzene-1,4-dicarboxylic acid, heptane-1,7-dicarboxylic acid, cyclobutane-1,1-dicarboxylic acid, 1,14-tetradecanedicarboxylic acid, 5,6-dehydronorbornane-2,3-dicarboxylic acid, 5-ethyl-2,3-pyridinedicarboxylic acid or camphordicarboxylic acid, tricarboxylic acids such as 2-hydroxy-1,2,3-propanetricarboxylic acid, 7-chloro-2,3,8-quinolinetricarboxylic acid, 1,2,3-, 1,2,4-benzenetricarboxylic acid, 1,2,4-butanetricarboxylic acid, 2-phosphono-1,2,4-butanetricarboxylic acid, 1,3,5-benzenetricarboxylic acid, 1-hydroxy-1,2,3-propanetricarboxylic acid, 4,5-dihydro-4,5-dioxo-1H-pyrrolo[2,3-F]quinoline-2,7,9-tricarboxylic acid, 5-acetyl-3-amino-6-methylbenzene-1,2,4-tricarboxylic acid, 3-amino-5-benzoyl-6-methylbenzene-1,2,4-tricarboxylic acid, 1,2,3-propanetricarboxylic acid or aurintricarboxylic acid, or tetracarboxylic acids such as 1,1-dioxidoperylo[1,12-BCD]thiophene-3,4,9,10-tetracarboxylic acid, perylene-tetracarboxylic acids such as perylene-3,4,9,10-tetracarboxylic acid or (perylene 1,12-sulfone)-3,4,9,10-tetracarboxylic acid, butanetetracarboxylic acids such as 1,2,3,4-butanetetracarboxylic acid or meso-1,2,3,4-butanetetracarboxylic acid, decane-2,4,6,8-tetracarboxylic acid, 1,4,7,10,13,16-hexaoxacyclooctadecane-2,3,11,12-tetracarboxylic acid, 1,2,4,5-benzenetetracarboxylic acid, 1,2,11,12-dodecanetetracarboxylic acid, 1,2,5,6-hexanetetracarboxylic acid, 1,2,7,8-octanetetracarboxylic acid, 1,4,5,8-naphthalenetetracarboxylic acid, 1,2,9,10-decanetetracarboxylic acid, benzophenone-tetracarboxylic acid, 3,3',4,4'-benzophenonetetracarboxylic acid, tetrahydrofuran-tetracarboxylic acid or cyclopentanetetracarboxylic acids such as cyclopentane-1,2,3,4-tetracarboxylic acid.

Very particular preference is given to using optionally at least monosubstituted aromatic dicarboxylic, tricarboxylic or tetracarboxylic acids which have one, two, three, four or more rings and in which each of the rings can comprise at least one heteroatom, with two or more rings being able to comprise identical or different heteroatoms. For example, preference is given to one-ring dicarboxylic acids, one-ring tricarboxylic acids, one-ring tetracarboxylic acids, two-ring dicarboxylic acids, two-ring tricarboxylic acids, two-ring tetracarboxylic acids, three-ring dicarboxylic acids, three-ring tricarboxylic acids, three-ring tetracarboxylic acids, four-ring dicarboxylic acids, four-ring tricarboxylic acids and/or four-ring tetracarboxylic acids. Suitable heteroatoms are, for example, N, O, S, B, P, and preferred heteroatoms here are N, S and/or O, Suitable substituents which may be mentioned in this respect are, inter alia, —OH, a nitro group, an amino group or an alkyl or alkoxy group.

Particular preference is given to using acetylenedicarboxylic acid (ADC), camphordicarboxylic acid, fumaric acid, succinic acid, benzenedicarboxylic acids, naphthalenedicarboxylic acids, biphenyldicarboxylic acids such as 4,4'-biphenyldicarboxylic acid (BPDC), pyrazinedicarboxylic acids such as 2,5-pyrazinedicarboxylic acid, bipyridinedicarboxylic acids such as 2,2'-bipyridinedicarboxylic acids such as 2,2'-bipyridine-5,5'-dicarboxylic acid, benzenetricarboxylic acids such as 1,2,3-, 1,2,4-benzenetricarboxylic acid or 1,3,5-benzenetricarboxylic acid (BTC), benzenetetracarboxylic acid, adamantane-tetracarboxylic acid (ATC), adamantanedibenzoate (ADB), benzenetribenzoate (BTB), methanetetrabenzoate (MTB), adamantanetetrabenzoate or dihydroxyterephthalic acids such as 2,5-dihydroxyterephthalic acid (DHBDC) as at least bidentate organic compounds.

Very particular preference is given to using, inter alia, isophthalic acid, terephthalic acid, 2,5-dihydroxyterephthalic acid, 1,2,3-benzenetricarboxylic acid, 1,3,5-benzenetricarboxylic acid, 2,6-naphthalenedicarboxylic acid, 1,4-naphthalenedicarboxylic acid, 1,2,3,4- and 1,2,4,5-benzenetetracarboxylic acid, camphordicarboxylic acid or 2,2'-bipyridine-5,5'-dicarboxylic acid.

Apart from these at least bidentate organic compounds, the metal organic framework can further comprise one or more monodentate ligands.

Examples of metal organic frameworks known in the prior art are given below. In addition to the designation of the MOF, the metal and the at least bidentate ligand, the solvent and the cell parameters (angles α, β and γ and the dimensions A, B and C in Å) are indicated. The latter were determined by X-ray diffraction.

| MOF-n | Constituents molar ratio M + L | Solvents | α | β | γ | a | b | c | Space group |
|---|---|---|---|---|---|---|---|---|---|
| MOF-0 | $Zn(NO_3)_2 \cdot 6H_2O$<br>$H_3(BTC)$ | ethanol | 90 | 90 | 120 | 16.711 | 16.711 | 14.189 | P6(3)/Mcm |
| MOF-2 | $Zn(NO_3)_2 \cdot 6H_2O$<br>(0.246 mmol)<br>$H_2(BDC)$<br>0.241 mmol | DMF<br>toluene | 90 | 102.8 | 90 | 6.718 | 15.49 | 12.43 | P2(1)/n |
| MOF-3 | $Zn(NO_3)_2 \cdot 6H_2O$<br>(1.89 mmol)<br>$H_2(BDC)$<br>(1.93 mmol) | DMF<br>MeOH | 99.72 | 111.11 | 108.4 | 9.726 | 9.911 | 10.45 | P-1 |
| MOF-4 | $Zn(NO_3)_2 \cdot 6H_2O$<br>(1.00 mmol)<br>$H_3(BTC)$<br>(0.5 mmol) | ethanol | 90 | 90 | 90 | 14.728 | 14.728 | 14.728 | P2(1)3 |
| MOF-5 | $Zn(NO_3)_2 \cdot 6H_2O$<br>(2.22 mmol)<br>$H_2(BDC)$<br>(2.17 mmol) | DMF<br>chlorobenzene | 90 | 90 | 90 | 25.669 | 25.669 | 25.669 | Fm-3m |
| MOF-38 | $Zn(NO_3)_2 \cdot 6H_2O$<br>(0.27 mmol)<br>$H_3(BTC)$<br>(0.15 mmol) | DMF<br>chlorobenzene | 90 | 90 | 90 | 20.657 | 20.657 | 17.84 | I4cm |
| MOF-31<br>$Zn(ADC)_2$ | $Zn(NO_3)_2 \cdot 6H_2O$<br>0.4 mmol<br>$H_2(ADC)$<br>0.8 mmol | ethanol | 90 | 90 | 90 | 10.821 | 10.821 | 10.821 | Pn(-3)m |
| MOF-12<br>$Zn_2(ATC)$ | $Zn(NO_3)_2 \cdot 6H_2O$<br>0.3 mmol<br>$H_4(ATC)$<br>0.15 mmol | ethanol | 90 | 90 | 90 | 15.745 | 16.907 | 18.167 | Pbca |
| MOF-20<br>ZnNDC | $Zn(NO_3)_2 \cdot 6H_2O$<br>0.37 mmol<br>$H_2NDC$<br>0.36 mmol | DMF<br>chlorobenzene | 90 | 92.13 | 90 | 8.13 | 16.444 | 12.807 | P2(1)/c |
| MOF-37 | $Zn(NO_3)_2 \cdot 6H_2O$<br>0.2 mmol<br>$H_2NDC$<br>0.2 mmol | DEF<br>chlorobenzene | 72.38 | 83.16 | 84.33 | 9.952 | 11.576 | 15.556 | P-1 |

-continued

| MOF-n | Constituents molar ratio M + L | Solvents | α | β | γ | a | b | c | Space group |
|---|---|---|---|---|---|---|---|---|---|
| MOF-8 Tb₂(ADC) | Tb(NO₃)₃·5H₂O 0.10 mmol H₂ADC 0.20 mmol | DMSO MeOH | 90 | 115.7 | 90 | 19.83 | 9.822 | 19.183 | C2/c |
| MOF-9 Tb₂(ADC) | Tb(NO₃)₃·5H₂O 0.08 mmol H₂ADB 0.12 mmol | DMSO | 90 | 102.09 | 90 | 27.056 | 16.795 | 28.139 | C2/c |
| MOF-6 | Tb(NO₃)₃·5H₂O 0.30 mmol H₂(BDC) 0.30 mmol | DMF MeOH | 90 | 91.28 | 90 | 17.599 | 19.996 | 10.545 | P21/c |
| MOF-7 | Tb(NO₃)₃·5H₂O 0.15 mmol H₂(BDC) 0.15 mmol | H₂O | 102.3 | 91.12 | 101.5 | 6.142 | 10.069 | 10.096 | P-1 |
| MOF-69A | Zn(NO₃)₂·6H₂O 0.083 mmol 4,4'-BPDC 0.041 mmol | DEF H₂O₂ MeNH₂ | 90 | 111.6 | 90 | 23.12 | 20.92 | 12 | C2/c |
| MOF-69B | Zn(NO₃)₂·6H₂O 0.083 mmol 2,6-NCD 0.041 mmol | DEF H₂O₂ MeNH₂ | 90 | 95.3 | 90 | 20.17 | 18.55 | 12.16 | C2/c |
| MOF-11 Cu₂(ATC) | Cu(NO₃)₂·2.5H₂O 0.47 mmol H₂ATC 0.22 mmol | H₂O | 90 | 93.86 | 90 | 12.987 | 11.22 | 11.336 | C2/c |
| MOF-11 Cu₂(ATC) dehydr. | | | 90 | 90 | 90 | 8.4671 | 8.4671 | 14.44 | P42/mmc |
| MOF-14 Cu₃(BTB) | Cu(NO₃)₂·2.5H₂O 0.28 mmol H₃BTB 0.052 mmol | H₂O DMF EtOH | 90 | 90 | 90 | 26.946 | 26.946 | 26.946 | Im-3 |
| MOF-32 Cd(ATC) | Cd(NO₃)₂·4H₂O 0.24 mmol H₄ATC 0.10 mmol | H₂O NaOH | 90 | 90 | 90 | 13.468 | 13.468 | 13.468 | P(−4)3m |
| MOF-33 Zn₂(ATB) | ZnCl₂ 0.15 mmol H₄ATB 0.02 mmol | H₂O DMF EtOH | 90 | 90 | 90 | 19.561 | 15.255 | 23.404 | Imma |
| MOF-34 Ni(ATC) | Ni(NO₃)₂·6H₂O 0.24 mmol H₄ATC 0.10 mmol | H₂O NaOH | 90 | 90 | 90 | 10.066 | 11.163 | 19.201 | P2₁2₁2₁ |
| MOF-36 Zn₂(MTB) | Zn(NO₃)₂·4H₂O 0.20 mmol H₄MTB 0.04 mmol | H₂O DMF | 90 | 90 | 90 | 15.745 | 16.907 | 18.167 | Pbca |
| MOF-39 Zn₃O(HBTB) | Zn(NO₃)₂4H₂O 0.27 mmol H₃BTB 0.07 mmol | H₂O DMF EtOH | 90 | 90 | 90 | 17.158 | 21.591 | 25.308 | Pnma |
| NO305 | FeCl₂·4H₂O 5.03 mmol formic acid 86.90 mmol | DMF | 90 | 90 | 120 | 8.2692 | 8.2692 | 63.566 | R-3c |
| NO306A | FeCl₂·4H₂O 5.03 mmol formic acid 86.90 mmol | DEF | 90 | 90 | 90 | 9.9364 | 18.374 | 18.374 | Pbcn |
| NO29 MOF-0 similar | Mn(Ac)₂·4H₂O 0.46 mmol H₃BTC 0.69 mmol | DMF | 120 | 90 | 90 | 14.16 | 33.521 | 33.521 | P-1 |
| BPR48 A2 | Zn(NO₃)₂6H₂O 0.012 mmol H₂BDC 0.012 mmol | DMSO toluene | 90 | 90 | 90 | 14.5 | 17.04 | 18.02 | Pbca |
| BPR69 B1 | Cd(NO₃)₂4H₂O 0.0212 mmol H₂BDC 0.0428 mmol | DMSO | 90 | 98.76 | 90 | 14.16 | 15.72 | 17.66 | Cc |

-continued

| MOF-n | Constituents molar ratio M + L | Solvents | α | β | γ | a | b | c | Space group |
|---|---|---|---|---|---|---|---|---|---|
| BPR92 A2 | Co(NO$_3$)$_2$·6H$_2$O 0.018 mmol H$_2$BDC 0.018 mmol | NMP | 106.3 | 107.63 | 107.2 | 7.5308 | 10.942 | 11.025 | P1 |
| BPR95 C5 | Cd(NO$_3$)$_2$4H$_2$O 0.012 mmol H$_2$BDC 0.36 mmol | NMP | 90 | 112.8 | 90 | 14.460 | 11.085 | 15.829 | P2(1)/n |
| CuC$_6$H$_4$O$_6$ | Cu(NO$_3$)$_2$·2.5H$_2$O 0.370 mmol H$_2$BDC(OH)$_2$ 0.37 mmol | DMF chloro-benzene | 90 | 105.29 | 90 | 15.259 | 14.816 | 14.13 | P2(1)/c |
| M(BTC) MOF-0 similar | Co(SO$_4$) H$_2$O 0.055 mmol H$_3$BTC 0.037 mmol | DMF | | as for MOF-0 | | | | | |
| Tb(C$_6$H$_4$O$_6$) | Tb(NO$_3$)$_3$·5H$_2$O 0.370 mmol H$_2$(C$_6$H$_4$O$_6$) 0.56 mmol | DMF chloro-benzene | 104.6 | 107.9 | 97.147 | 10.491 | 10.981 | 12.541 | P-1 |
| Zn(C$_2$O$_4$) | ZnCl$_2$ 0.370 mmol oxalic acid 0.37 mmol | DMF chloro-benzene | 90 | 120 | 90 | 9.4168 | 9.4168 | 8.464 | P(−3)1m |
| Co(CHO) | Co(NO$_3$)$_2$·5H$_2$O 0.043 mmol formic acid 1.60 mmol | DMF | 90 | 91.32 | 90 | 11.328 | 10.049 | 14.854 | P2(1)/n |
| Cd(CHO) | Cd(NO$_3$)$_2$·4H$_2$O 0.185 mmol formic acid 0.185 mmol | DMF | 90 | 120 | 90 | 8.5168 | 8.5168 | 22.674 | R-3c |
| Cu(C$_3$H$_2$O$_4$) | Cu(NO$_3$)$_2$·2.5H$_2$O 0.043 mmol malonic acid 0.192 mmol | DMF | 90 | 90 | 90 | 8.366 | 8.366 | 11.919 | P43 |
| Zn$_6$(NDC)$_5$ MOF-48 | Zn(NO$_3$)$_2$·6H$_2$O 0.097 mmol 14 NDC 0.069 mmol | DMF chloro-benzene H$_2$O$_2$ | 90 | 95.902 | 90 | 19.504 | 16.482 | 14.64 | C2/m |
| MOF-47 | Zn(NO$_3$)$_2$6H$_2$O 0.185 mmol H$_2$(BDC[CH$_3$]$_4$) 0.185 mmol | DMF chloro-benzene H$_2$O$_2$ | 90 | 92.55 | 90 | 11.303 | 16.029 | 17.535 | P2(1)/c |
| MO25 | Cu(NO$_3$)$_2$·2.5H$_2$O 0.084 mmol BPhDC 0.085 mmol | DMF | 90 | 112.0 | 90 | 23.880 | 16.834 | 18.389 | P2(1)/c |
| Cu-thio | Cu(NO$_3$)$_2$·2.5H$_2$O 0.084 mmol thiophenedicarboxylic acid 0.085 mmol | DEF | 90 | 113.6 | 90 | 15.4747 | 14.514 | 14.032 | P2(1)/c |
| ClBDC1 | Cu(NO$_3$)$_2$·2.5H$_2$O 0.084 mmol H$_2$(BDCCl$_2$) 0.085 mmol | DMF | 90 | 105.6 | 90 | 14.911 | 15.622 | 18.413 | C2/c |
| MOF-101 | Cu(NO$_3$)$_2$·2.5H$_2$O 0.084 mmol BrBDC 0.085 mmol | DMF | 90 | 90 | 90 | 21.607 | 20.607 | 20.073 | Fm3m |
| Zn$_3$(BTC)$_2$ | ZnCl$_2$ 0.033 mmol H$_3$BTC 0.033 mmol | DMF EtOH base added | 90 | 90 | 90 | 26.572 | 26.572 | 26.572 | Fm-3m |
| MOF-j | Co(CH$_3$CO$_2$)$_2$·4H$_2$O (1.65 mmol) H$_3$(BZC) (0.95 mmol) | H$_2$O | 90 | 112.0 | 90 | 17.482 | 12.963 | 6.559 | C2 |
| MOF-n | Zn(NO$_3$)$_2$·6H$_2$O H$_3$(BTC) | ethanol | 90 | 90 | 120 | 16.711 | 16.711 | 14.189 | P6(3)/mcm |
| PbBDC | Pb(NO$_3$)$_2$ (0.181 mmol) H$_2$(BDC) (0.181 mmol) | DMF ethanol | 90 | 102.7 | 90 | 8.3639 | 17.991 | 9.9617 | P2(1)/n |

-continued

| MOF-n | Constituents molar ratio M + L | Solvents | α | β | γ | a | b | c | Space group |
|---|---|---|---|---|---|---|---|---|---|
| Znhex | Zn(NO$_3$)$_2$•6H$_2$O (0.171 mmol) H$_3$BTB (0.114 mmol) | DMF p-xylene ethanol | 90 | 90 | 120 | 37.1165 | 37.117 | 30.019 | P3(1)c |
| AS16 | FeBr$_2$ 0.927 mmol H$_2$(BDC) 0.927 mmol | DMF anhydr. | 90 | 90.13 | 90 | 7.2595 | 8.7894 | 19.484 | P2(1)c |
| AS27-2 | FeBr$_2$ 0.927 mmol H$_3$(BDC) 0.464 mmol | DMF anhydr. | 90 | 90 | 90 | 26.735 | 26.735 | 26.735 | Fm3m |
| AS32 | FeCl$_3$ 1.23 mmol H$_2$(BDC) 1.23 mmol | DMF anhydr. ethanol | 90 | 90 | 120 | 12.535 | 12.535 | 18.479 | P6(2)c |
| AS54-3 | FeBr$_2$ 0.927 BPDC 0.927 mmol | DMF anhydr. n-propanol | 90 | 109.98 | 90 | 12.019 | 15.286 | 14.399 | C2 |
| AS61-4 | FeBr$_2$ 0.927 mmol m-BDC 0.927 mmol | pyridine anhydr. | 90 | 90 | 120 | 13.017 | 13.017 | 14.896 | P6(2)c |
| AS68-7 | FeBr$_2$ 0.927 mmol m-BDC 1.204 mmol | DMF anhydr. pyridine | 90 | 90 | 90 | 18.3407 | 10.036 | 18.039 | Pca2$_1$ |
| Zn(ADC) | Zn(NO$_3$)$_2$•6H$_2$O 0.37 mmol H$_2$(ADC) 0.36 mmol | DMF chloro-benzene | 90 | 99.85 | 90 | 16.764 | 9.349 | 9.635 | C2/c |
| MOF-12 Zn$_2$(ATC) | Zn(NO$_3$)$_2$•6H$_2$O 0.30 mmol H$_4$(ATC) 0.15 mmol | ethanol | 90 | 90 | 90 | 15.745 | 16.907 | 18.167 | Pbca |
| MOF-20 ZnNDC | Zn(NO$_3$)$_2$•6H$_2$O 0.37 mmol H$_2$NDC 0.36 mmol | DMF chloro-benzene | 90 | 92.13 | 90 | 8.13 | 16.444 | 12.807 | P2(1)/c |
| MOF-37 | Zn(NO$_3$)$_2$•6H$_2$O 0.20 mmol H$_2$NDC 0.20 mmol | DEF chloro-benzene | 72.38 | 83.16 | 84.33 | 9.952 | 11.576 | 15.556 | P-1 |
| Zn(NDC) (DMSO) | Zn(NO$_3$)$_2$•6H$_2$O H$_2$NDC | DMSO | 68.08 | 75.33 | 88.31 | 8.631 | 10.207 | 13.114 | P-1 |
| Zn(NDC) | Zn(NO$_3$)$_2$•6H$_2$O H$_2$NDC | | 90 | 99.2 | 90 | 19.289 | 17.628 | 15.052 | C2/c |
| Zn(HPDC) | Zn(NO$_3$)$_2$•4H$_2$O 0.23 mmol H$_2$(HPDC) 0.05 mmol | DMF H$_2$O | 107.9 | 105.06 | 94.4 | 8.326 | 12.085 | 13.767 | P-1 |
| Co(HPDC) | Co(NO$_3$)$_2$•6H$_2$O 0.21 mmol H$_2$(HPDC) 0.06 mmol | DMF H$_2$O/ ethanol | 90 | 97.69 | 90 | 29.677 | 9.63 | 7.981 | C2/c |
| Zn$_3$(PDC)2.5 | Zn(NO$_3$)$_2$•4H$_2$O 0.17 mmol H$_2$(HPDC) 0.05 mmol | DMF/ ClBz H$_2$O/ TEA | 79.34 | 80.8 | 85.83 | 8.564 | 14.046 | 26.428 | P-1 |
| Cd$_2$(TPDC)2 | Cd(NO$_3$)$_2$•4H$_2$O 0.06 mmol H$_2$(HPDC) 0.06 mmol | methanol/ CHP H$_2$O | 70.59 | 72.75 | 87.14 | 10.102 | 14.412 | 14.964 | P-1 |
| Tb(PDC)1.5 | Tb(NO$_3$)$_3$•5H$_2$O 0.21 mmol H$_2$(PDC) 0.034 mmol | DMF H$_2$O/ ethanol | 109.8 | 103.61 | 100.14 | 9.829 | 12.11 | 14.628 | P-1 |
| ZnDBP | Zn(NO$_3$)$_2$•6H$_2$O 0.05 mmol dibenzyl phosphate 0.10 mmol | MeOH | 90 | 93.67 | 90 | 9.254 | 10.762 | 27.93 | P2/n |

-continued

| MOF-n | Constituents molar ratio M + L | Solvents | α | β | γ | a | b | c | Space group |
|---|---|---|---|---|---|---|---|---|---|
| Zn$_3$(BPDC) | ZnBr$_2$ 0.021 mmol 4,4'BPDC 0.005 mmol | DMF | 90 | 102.76 | 90 | 11.49 | 14.79 | 19.18 | P21/n |
| CdBDC | Cd(NO$_3$)$_2$•4H$_2$O 0.100 mmol H$_2$(BDC) 0.401 mmol | DMF Na$_2$SiO$_3$ (aq) | 90 | 95.85 | 90 | 11.2 | 11.11 | 16.71 | P21/n |
| Cd-mBDC | Cd(NO$_3$)$_2$•4H$_2$O 0.009 mmol H$_2$(mBDC) 0.018 mmol | DMF MeNH$_2$ | 90 | 101.1 | 90 | 13.69 | 18.25 | 14.91 | C2/c |
| Zn$_4$OBNDC | Zn(NO$_3$)$_2$•6H$_2$O 0.041 mmol BNDC | DEF MeNH$_2$ H$_2$O$_2$ | 90 | 90 | 90 | 22.35 | 26.05 | 59.56 | Fmmm |
| Eu(TCA) | Eu(NO$_3$)$_3$•6H$_2$O 0.14 mmol TCA 0.026 mmol | DMF chlorobenzene | 90 | 90 | 90 | 23.325 | 23.325 | 23.325 | Pm-3n |
| Tb(TCA) | Tb(NO$_3$)$_3$•6H$_2$O 0.069 mmol TCA 0.026 mmol | DMF chlorobenzene | 90 | 90 | 90 | 23.272 | 23.272 | 23.372 | Pm-3n |
| Formates | Ce(NO$_3$)$_3$•6H$_2$O 0.138 mmol formic acid 0.43 mmol | H$_2$O ethanol | 90 | 90 | 120 | 10.668 | 10.667 | 4.107 | R-3m |
|  | FeCl$_2$•4H$_2$O 5.03 mmol formic acid 86.90 mmol | DMF | 90 | 90 | 120 | 8.2692 | 8.2692 | 63.566 | R-3c |
|  | FeCl$_2$•4H$_2$O 5.03 mmol formic acid 86.90 mmol | DEF | 90 | 90 | 90 | 9.9364 | 18.374 | 18.374 | Pbcn |
|  | FeCl$_2$•4H$_2$O 5.03 mmol formic acid 86.90 mmol | DEF | 90 | 90 | 90 | 8.335 | 8.335 | 13.34 | P-31c |
| NO330 | FeCl$_2$•4H$_2$O 0.50 mmol formic acid 8.69 mmol | formamide | 90 | 90 | 90 | 8.7749 | 11.655 | 8.3297 | Pnna |
| NO332 | FeCl$_2$•4H$_2$O 0.50 mmol formic acid 8.69 mmol | DIP | 90 | 90 | 90 | 10.0313 | 18.808 | 18.355 | Pbcn |
| NO333 | FeCl$_2$•4H$_2$O 0.50 mmol formic acid 8.69 mmol | DBF | 90 | 90 | 90 | 45.2754 | 23.861 | 12.441 | Cmcm |
| NO335 | FeCl$_2$•4H$_2$O 0.50 mmol formic acid 8.69 mmol | CHF | 90 | 91.372 | 90 | 11.5964 | 10.187 | 14.945 | P21/n |
| NO336 | FeCl$_2$•4H$_2$O 0.50 mmol formic acid 8.69 mmol | MFA | 90 | 90 | 90 | 11.7945 | 48.843 | 8.4136 | Pbcm |
| NO13 | Mn(Ac)$_2$•4H$_2$O 0.46 mmol benzoic acid 0.92 mmol bipyridine 0.46 mmol | ethanol | 90 | 90 | 90 | 18.66 | 11.762 | 9.418 | Pbcn |
| NO29 MOF-0 similar | Mn(Ac)$_2$•4H$_2$O 0.46 mmol H$_3$BTC 0.69 mmol | DMF | 120 | 90 | 90 | 14.16 | 33.521 | 33.521 | P-1 |
| Mn(hfac)$_2$ (O$_2$CC$_6$H$_5$) | Mn(Ac)$_2$•4H$_2$O 0.46 mmol Hfac 0.92 mmol bipyridine 0.46 mmol | ether | 90 | 95.32 | 90 | 9.572 | 17.162 | 14.041 | C2/c |

-continued

| MOF-n | Constituents molar ratio M + L | Solvents | α | β | γ | a | b | c | Space group |
|---|---|---|---|---|---|---|---|---|---|
| BPR43G2 | $Zn(NO_3)_2 \cdot 6H_2O$ 0.0288 mmol $H_2BDC$ 0.0072 mmol | DMF $CH_3CN$ | 90 | 91.37 | 90 | 17.96 | 6.38 | 7.19 | C2/c |
| BPR48A2 | $Zn(NO_3)_2 6H_2O$ 0.012 mmol $H_2BDC$ 0.012 mmol | DMSO toluene | 90 | 90 | 90 | 14.5 | 17.04 | 18.02 | Pbca |
| BPR49B1 | $Zn(NO_3)_2 6H_2O$ 0.024 mmol $H_2BDC$ 0.048 mmol | DMSO methanol | 90 | 91.172 | 90 | 33.181 | 9.824 | 17.884 | C2/c |
| BPR56E1 | $Zn(NO_3)_2 6H_2O$ 0.012 mmol $H_2BDC$ 0.024 mmol | DMSO n-propanol | 90 | 90.096 | 90 | 14.5873 | 14.153 | 17.183 | P2(1)/n |
| BPR68D10 | $Zn(NO_3)_2 6H_2O$ 0.0016 mmol $H_3BTC$ 0.0064 mmol | DMSO benzene | 90 | 95.316 | 90 | 10.0627 | 10.17 | 16.413 | P2(1)/c |
| BPR69B1 | $Cd(NO_3)_2 4H_2O$ 0.0212 mmol $H_2BDC$ 0.0428 mmol | DMSO | 90 | 98.76 | 90 | 14.16 | 15.72 | 17.66 | Cc |
| BPR73E4 | $Cd(NO_3)_2 4H_2O$ 0.006 mmol $H_2BDC$ 0.003 mmol | DMSO toluene | 90 | 92.324 | 90 | 8.7231 | 7.0568 | 18.438 | P2(1)/n |
| BPR76D5 | $Zn(NO_3)_2 6H_2O$ 0.0009 mmol $H_2BzPDC$ 0.0036 mmol | DMSO | 90 | 104.17 | 90 | 14.4191 | 6.2599 | 7.0611 | Pc |
| BPR80B5 | $Cd(NO_3)_2 \cdot 4H_2O$ 0.018 mmol $H_2BDC$ 0.036 mmol | DMF | 90 | 115.11 | 90 | 28.049 | 9.184 | 17.837 | C2/c |
| BPR80H5 | $Cd(NO_3)_2 4H_2O$ 0.027 mmol $H_2BDC$ 0.027 mmol | DMF | 90 | 119.06 | 90 | 11.4746 | 6.2151 | 17.268 | P2/c |
| BPR82C6 | $Cd(NO_3)_2 4H_2O$ 0.0068 mmol $H_2BDC$ 0.202 mmol | DMF | 90 | 90 | 90 | 9.7721 | 21.142 | 27.77 | Fdd2 |
| BPR86C3 | $Co(NO_3)_2 6H_2O$ 0.0025 mmol $H_2BDC$ 0.075 mmol | DMF | 90 | 90 | 90 | 18.3449 | 10.031 | 17.983 | Pca2(1) |
| BPR86H6 | $Cd(NO_3)_2 \cdot 6H_2O$ 0.010 mmol $H_2BDC$ 0.010 mmol | DMF | 80.98 | 89.69 | 83.412 | 9.8752 | 10.263 | 15.362 | P-1 |
|  | $Co(NO_3)_2 6H_2O$ | NMP | 106.3 | 107.63 | 107.2 | 7.5308 | 10.942 | 11.025 | P1 |
| BPR95A2 | $Zn(NO_3)_2 6H_2O$ 0.012 mmol $H_2BDC$ 0.012 mmol | NMP | 90 | 102.9 | 90 | 7.4502 | 13.767 | 12.713 | P2(1)/c |
| $CuC_6F_4O_4$ | $Cu(NO_3)_2 \cdot 2.5H_2O$ 0.370 mmol $H_2BDC(OH)_2$ 0.37 mmol | DMF chlorobenzene | 90 | 98.834 | 90 | 10.9675 | 24.43 | 22.553 | P2(1)/n |
| Fe formic | $FeCl_2 \cdot 4H_2O$ 0.370 mmol formic acid 0.37 mmol | DMF | 90 | 91.543 | 90 | 11.495 | 9.963 | 14.48 | P2(1)/n |
| Mg formic | $Mg(NO_3)_2 \cdot 6H_2O$ 0.370 mmol formic acid 0.37 mmol | DMF | 90 | 91.359 | 90 | 11.383 | 9.932 | 14.656 | P2(1)/n |
| $MgC_6H_4O_6$ | $Mg(NO_3)_2 \cdot 6H_2O$ 0.370 mmol $H_2BDC(OH)_2$ 0.37 mmol | DMF | 90 | 96.624 | 90 | 17.245 | 9.943 | 9.273 | C2/c |

-continued

| MOF-n | Constituents molar ratio M + L | Solvents | α | β | γ | a | b | c | Space group |
|---|---|---|---|---|---|---|---|---|---|
| ZnC₂H₄BDC MOF-38 | ZnCl₂ 0.44 mmol CBBDC 0.261 mmol | DMF | 90 | 94.714 | 90 | 7.3386 | 16.834 | 12.52 | P2(1)/n |
| MOF-49 | ZnCl₂ 0.44 mmol m-BDC 0.261 mmol | DMF CH₃CN | 90 | 93.459 | 90 | 13.509 | 11.984 | 27.039 | P2/c |
| MOF-26 | Cu(NO₃)₂·5H₂O 0.084 mmol DCPE 0.085 mmol | DMF | 90 | 95.607 | 90 | 20.8797 | 16.017 | 26.176 | P2(1)/n |
| MOF-112 | Cu(NO₃)₂·2.5H₂O 0.084 mmol o-Br-m-BDC 0.085 mmol | DMF ethanol | 90 | 107.49 | 90 | 29.3241 | 21.297 | 18.069 | C2/c |
| MOF-109 | Cu(NO₃)₂·2.5H₂O 0.084 mmol KDB 0.085 mmol | DMF | 90 | 111.98 | 90 | 23.8801 | 16.834 | 18.389 | P2(1)/c |
| MOF-111 | Cu(NO₃)₂·2.5H₂O 0.084 mmol o-BrBDC 0.085 mmol | DMF ethanol | 90 | 102.16 | 90 | 10.6767 | 18.781 | 21.052 | C2/c |
| MOF-110 | Cu(NO₃)₂·2.5H₂O 0.084 mmol thiophene-dicarboxylic acid 0.085 mmol | DMF | 90 | 90 | 120 | 20.0652 | 20.065 | 20.747 | R-3/m |
| MOF-107 | Cu(NO₃)₂·2.5H₂O 0.084 mmol thiophene-dicarboxylic acid 0.085 mmol | DEF | 104.8 | 97.075 | 95.206 | 11.032 | 18.067 | 18.452 | P-1 |
| MOF-108 | Cu(NO₃)₂·2.5H₂O 0.084 mmol thiophene-dicarboxylic acid 0.085 mmol | DBF/ methanol | 90 | 113.63 | 90 | 15.4747 | 14.514 | 14.032 | C2/c |
| MOF-102 | Cu(NO₃)₂·2.5H₂O 0.084 mmol H₂(BDCCl₂) 0.085 mmol | DMF | 91.63 | 106.24 | 112.01 | 9.3845 | 10.794 | 10.831 | P-1 |
| Clbdc1 | Cu(NO₃)₂·2.5H₂O 0.084 mmol H₂(BDCCl₂) 0.085 mmol | DEF | 90 | 105.56 | 90 | 14.911 | 15.622 | 18.413 | P-1 |
| Cu(NMOP) | Cu(NO₃)₂·2.5H₂O 0.084 mmol NBDC 0.085 mmol | DMF | 90 | 102.37 | 90 | 14.9238 | 18.727 | 15.529 | P2(1)/m |
| Tb(BTC) | Tb(NO₃)₃·5H₂O 0.033 mmol H₃BTC 0.033 mmol | DMF | 90 | 106.02 | 90 | 18.6986 | 11.368 | 19.721 | |
| Zn₃(BTC)₂ Honk | ZnCl₂ 0.033 mmol H₃BTC 0.033 mmol | DMF ethanol | 90 | 90 | 90 | 26.572 | 26.572 | 26.572 | Fm-3m |
| Zn₄O(NDC) | Zn(NO₃)₂·4H₂O 0.066 mmol 14NDC 0.066 mmol | DMF ethanol | 90 | 90 | 90 | 41.5594 | 18.818 | 17.574 | aba2 |
| CdTDC | Cd(NO₃)₂·4H₂O 0.014 mmol thiophene 0.040 mmol DABCO 0.020 mmol | DMF H₂O | 90 | 90 | 90 | 12.173 | 10.485 | 7.33 | Pmma |
| IRMOF-2 | Zn(NO₃)₂·4H₂O 0.160 mmol o-Br-BDC 0.60 mmol | DEF | 90 | 90 | 90 | 25.772 | 25.772 | 25.772 | Fm-3m |

-continued

| MOF-n | Constituents molar ratio M + L | Solvents | α | β | γ | a | b | c | Space group |
|---|---|---|---|---|---|---|---|---|---|
| IRMOF-3 | Zn(NO$_3$)$_2$·4H$_2$O 0.20 mmol H$_2$N-BDC 0.60 mmol | DEF ethanol | 90 | 90 | 90 | 25.747 | 25.747 | 25.747 | Fm-3m |
| IRMOF-4 | Zn(NO$_3$)$_2$·4H$_2$O 0.11 mmol [C$_3$H$_7$O]$_2$-BDC 0.48 mmol | DEF | 90 | 90 | 90 | 25.849 | 25.849 | 25.849 | Fm-3m |
| IRMOF-5 | Zn(NO$_3$)$_2$·4H$_2$O 0.13 mmol [C$_5$H$_{11}$O]$_2$-BDC 0.50 mmol | DEF | 90 | 90 | 90 | 12.882 | 12.882 | 12.882 | Pm-3m |
| IRMOF-6 | Zn(NO$_3$)$_2$·4H$_2$O 0.20 mmol [C$_2$H$_4$]-BDC 0.60 mmol | DEF | 90 | 90 | 90 | 25.842 | 25.842 | 25.842 | Fm-3m |
| IRMOF-7 | Zn(NO$_3$)$_2$·4H$_2$O 0.07 mmol 1.4NDC 0.20 mmol | DEF | 90 | 90 | 90 | 12.914 | 12.914 | 12.914 | Pm-3m |
| IRMOF-8 | Zn(NO$_3$)$_2$·4H$_2$O 0.55 mmol 2.6NDC 0.42 mmol | DEF | 90 | 90 | 90 | 30.092 | 30.092 | 30.092 | Fm-3m |
| IRMOF-9 | Zn(NO$_3$)$_2$·4H$_2$O 0.05 mmol BPDC 0.42 mmol | DEF | 90 | 90 | 90 | 17.147 | 23.322 | 25.255 | Pnnm |
| IRMOF-10 | Zn(NO$_3$)$_2$·4H$_2$O 0.02 mmol BPDC 0.012 mmol | DEF | 90 | 90 | 90 | 34.281 | 34.281 | 34.281 | Fm-3m |
| IRMOF-11 | Zn(NO$_3$)$_2$·4H$_2$O 0.05 mmol HPDC 0.20 mmol | DEF | 90 | 90 | 90 | 24.822 | 24.822 | 56.734 | R-3m |
| IRMOF-12 | Zn(NO$_3$)$_2$·4H$_2$O 0.017 mmol HPDC 0.12 mmol | DEF | 90 | 90 | 90 | 34.281 | 34.281 | 34.281 | Fm-3m |
| IRMOF-13 | Zn(NO$_3$)$_2$·4H$_2$O 0.048 mmol PDC 0.31 mmol | DEF | 90 | 90 | 90 | 24.822 | 24.822 | 56.734 | R-3m |
| IRMOF-14 | Zn(NO$_3$)$_2$·4H$_2$O 0.17 mmol PDC 0.12 mmol | DEF | 90 | 90 | 90 | 34.381 | 34.381 | 34.381 | Fm-3m |
| IRMOF-15 | Zn(NO$_3$)$_2$·4H$_2$O 0.063 mmol TPDC 0.025 mmol | DEF | 90 | 90 | 90 | 21.459 | 21.459 | 21.459 | Im-3m |
| IRMOF-16 | Zn(NO$_3$)$_2$·4H$_2$O 0.0126 mmol TPDC 0.05 mmol | DEF NMP | 90 | 90 | 90 | 21.49 | 21.49 | 21.49 | Pm-3m |

ADC Acetylenedicarboxylic acid
NDC Naphthalenedicarboxylic acid
BDC Benzenedicarboxylic acid
ATC Adamantanetetracarboxylic acid
BTC Benzenetricarboxylic acid
BTB Benzenetribenzoic acid
MTB Methanetetrabenzoic acid
ATB Adamantanetetrabenzoic acid
ADB Adamantanedibenzoic acid Further MOFs are MOF-177, MOF-178, MOF-74, MOF-235, MOF-236, MOF-69 to 80, MOF-501, MOF-502, which are described in the literature.

For the purposes of the present invention, very particular preference is given to the IRMOFs, in particular IRMOF-1 (=MOF-5).

In the case of organoboron frameworks, an organic compound having at least two boronic groups takes the place of the metal ion. Here, the skeleton of the compound can, as above, be used for the at least bidentate organic compound indicated for the metal organic frameworks. However, it also has to have at least two boronic groups (—B(OH)$_2$). Mention may here be made by way of example of benzenediboronic acids, in particular benzene-1,2-diboronic acid. Each of the boronic groups reacts with at least one at least bifunctional organic compound which can in principle be used like the at least bidentate organic compound for the metal organic frameworks. Here, it is possible to use identical skeletons and the abovementioned functional groups. However, it is also possible to use boronic-acid-containing organic compounds which are identical to or different from the first compound having at least two boronic groups. The at least bifunctional organic compound is preferably an aromatic diol or polyol or diboronic or polyboronic acid. The COFs are thus made up of a first organic compound having at least two boronic groups and a second organic compound having at least two functional groups. In addition, it is possible to use further compounds which are not necessarily bifunctional or multifunctional.

The nonaqueous organic solvent is preferably a $C_{1-6}$-alkanol, dimethyl sulfoxide (DMSO), N,N-dimethylformamide (DMF), N,N-diethylformamide (DEF), N,N-dimethylacetamide (DMAc), acetonitrile, toluene, dioxane, benzene, chlorobenzene, methyl ethyl ketone (MEK), pyridine, tetrahydrofuran (THF), ethyl acetate, optionally halogenated $C_{1-200}$-alkane, sulfolane, glycol, N-methylpyrrolidone (NMP), gamma-butyrolactone, alicyclic alcohols such as cyclohexanol, ketones, such as acetone or acetylacetone, cycloketones such as cyclohexanone, sulfolene or mixtures thereof.

A $C_{1-6}$-alkanol is an alcohol having from 1 to 6 carbon atoms. Examples are methanol, ethanol, n-propanol, isopropanol, n-butanol, isobutanol, t-butanol, pentanol, hexanol and mixtures thereof.

An optionally halogenated $C_{1-200}$-alkane is an alkane which has from 1 to 200 carbon atoms and in which one or more up to all hydrogen atoms can be replaced by halogen, preferably chlorine or fluorine, in particular chlorine. Examples are chloroform, dichloromethane, tetrachloromethane, dichloroethane, hexane, heptane, octane and mixtures thereof.

Preferred solvents are DMF, DEF, DMAc and NMP. Particular preference is given to DMF.

The term "nonaqueous" preferably refers to a solvent which does not exceed a maximum water content of 10% by weight, more preferably 5% by weight, even more preferably 1% by weight, more preferably 0.1% by weight, particularly preferably 0.01% by weight, based on the total weight of the solvent.

The total maximum water content of the liquid phase of the reaction mixture prior to the reaction is preferably 10% by weight, more preferably 5% by weight and even more preferably 1% by weight. The total maximum water content at the end of the reaction is preferably not more 3% by weight, more preferably not more than 1% by weight and most preferably not more than 0.5% by weight.

The water content can be determined by methods with which those skilled in the art are familiar. The water content is preferably determined by the Karl-Fischer method (cf., for example, Römpp Chemie Lexikon vol. 3 (1995), p. 2161, Georg Thieme Verlag).

The term "solvent" refers to pure solvents and also mixtures of various solvents.

After the reaction, it is possible to carry out a plurality of work-up steps which are preferably carried out with exclusion of moisture. These can be filtration, washing, drying, extraction, calcination or shaping steps.

Particular preference is given to a calcination step. The temperature set here is typically more than 250° C., preferably from 300° C. to 400° C.

Any starting compounds remaining in the pores can be removed in the calcination step.

In addition thereto or as an alternative thereto, the removal of starting materials from the pores of the porous organic framework can be effected by treatment of the framework which has been formed with a nonaqueous solvent. Here, the starting material to be removed is leached out in a type of "extraction process" and, if appropriate, replaced by a solvent molecule in the framework. This mild method is particularly suitable when the starting materials are high-boiling compounds. The treatment is preferably carried out for at least 30 minutes and can typically be carried out for up to two days. This can occur at room temperature or elevated temperature. It is preferably carried out at elevated temperature, for example at least 40° C., preferably 60° C. Extraction at the boiling point of the solvent used (under reflux) is also preferred.

The treatment can be carried out in a simple vessel by slurrying and stirring the framework. It is also possible to use extraction apparatuses such as Soxhlet apparatuses, in particular industrial extraction apparatuses.

As suitable solvents, it is possible to use those mentioned above, i.e., for example, $C_{1-6}$-alkanol, dimethyl sulfoxide (DMSO), N,N-dimethylformamide (DMF), N,N-diethyl-formamide (DEF), acetonitrile, toluene, dioxane, benzene, chlorobenzene, methyl ethyl ketone (MEK), pyridine, tetrahydrofuran (THF), ethyl acetate, optionally halogenated $C_{1-200}$-alkane, sulfolane, glycol, N-methylpyrrolidone (NMP), gamma-butyrolactone, alicyclic alcohols such as cyclohexanol, ketones such as acetone or acetylacetone, cycloketones such as cyclohexanone or mixtures thereof.

Preference is given to methanol, ethanol, propanol, acetone, MEK and mixtures thereof.

A very particularly preferred extraction solvent is methanol.

The solvent used for the extraction can be identical to or different from that for the reaction of the at least one metal compound with the at least one at least bidentate organic compound. In particular, it is not absolutely necessary but is preferred for the solvent in the "extraction" to be water-free.

The organic framework can be present in powder form or as agglomerates. The framework can be used as such or is converted into a shaped body.

Preferred processes for producing shaped bodies are extrusion or tableting. In the production of shaped bodies, the framework can be mixed with further materials such as binders, lubricants or other additives which are added during production. It is likewise conceivable for the framework to be mixed with further constituents, for example adsorbents such as activated carbon or the like.

The possible geometries of the shaped body are in principle not subject to any restrictions. For example, possible shapes are, inter alia, pellets such as disk-shaped pellets, pills, spheres, granules, extrudates such as rods, honeycombs, grids or hollow bodies.

To produce these shaped bodies, it is in principle possible to employ all suitable methods. In particular, the following processes are preferred:

Kneading/pan milling of the framework either alone or together with at least one binder and/or at least one pasting agent and/or at least one template compound to give a mixture; shaping of the resulting mixture by means of at least one suitable method such as extrusion; optionally washing and/or drying and/or calcination of the extrudate; optionally finishing treatment.

Tableting together with at least one binder and/or another auxiliary.

Application of the framework to at least one optionally porous support material. The material obtained can then be processed further by the above-described method to give a shaped body.

Application of the framework to at least one optionally porous substrate.

Kneading/pan milling and shaping can be carried out by any suitable method, for example as described in Ullmanns Enzyklopädie der Technischen Chemie, 4th edition, volume 2, p. 313 ff. (1972).

For example, the kneading/pan milling and/or shaping can be carried out by means of a piston press, roller press in the presence or absence of at least one binder, compounding, pelletization, tableting, extrusion, coextrusion, foaming, spinning, coating, granulation, preferably spray granulation, spraying, spray drying or a combination of two or more of these methods.

Very particular preference is given to producing pellets and/or tablets.

The kneading and/or shaping can be carried out at elevated temperatures, for example in the range from room temperature to 300° C., and/or under superatmospheric pressure, for example in the range from atmospheric pressure to a few hundred bar, and/or in a protective gas atmosphere, for example in the presence of at least one noble gas, nitrogen or a mixture of two or more thereof.

The kneading and/or shaping is, in a further embodiment, carried out with addition of at least one binder, with the binder used basically being able to be any chemical compound which ensures the desired viscosity for the kneading and/or shaping of the composition to be kneaded and/or shaped. Accordingly, binders can, for the purposes of the present invention, be either viscosity-increasing or viscosity-reducing compounds.

Preferred binders are, for example, inter alia aluminum oxide or binders comprising aluminum oxide, as are described, for example, in WO 94/29408, silicon dioxide as described, for example, in EP 0 592 050 A1, mixtures of silicon dioxide and aluminum oxide, as are described, for example, in WO 94/13584, clay minerals as described, for example, in JP 03-037156 A, for example montmorillonite, kaolin, bentonite, halloysite, dickite, nacrite and anauxite, alkoxysilanes as described, for example, in EP 0 102 544 B1, for example tetraalkoxysilanes such as tetramethoxysilane, tetraethoxysilane, tetrapropoxysilane, tetrabutoxysilane, or, for example, trialkoxysilanes such as trimethoxysilane, triethoxysilane, tripropoxysilane, tributoxysilane, alkoxytitanates, for example tetraalkoxytitanates such as tetramethoxytitanate, tetraethoxytitanate, tetrapropoxytitanate, tetrabutoxytitanate, or, for example, trialkoxytitanates such as trimethoxytitanate, triethoxytitanate, tripropoxytitanate, tributoxytitanate, alkoxyzirconates, for example tetraalkoxyzirconates such as tetramethoxyzirconate, tetraethoxyzirconate, tetrapropoxyzirconate, tetrabutoxyzirconate, or, for example, trialkoxyzirconates such as trimethoxyzirconate, triethoxyzirconate, tripropoxyzirconate, tributoxyzirconate, silica sols, amphiphilic substances and/or graphites.

As viscosity-increasing compound, it is, for example, also possible to use, if appropriate in addition to the abovementioned compounds, an organic compound and/or a hydrophilic polymer such as cellulose or a cellulose derivative such as methylcellulose and/or a polyacrylate and/or a polymethacrylate and/or a polyvinyl alcohol and/or a polyvinylpyrrolidone and/or a polyisobutene and/or a polytetrahydrofuran and/or a polyethylene oxide.

As pasting agent, it is possible to use, inter alia, preferably water or at least one alcohol such as a monoalcohol having from 1 to 4 carbon atoms, for example methanol, ethanol, n-propanol, isopropanol, 1-butanol, 2-butanol, 2-methyl-1-propanol or 2-methyl-2-propanol or a mixture of water and at least one of the alcohols mentioned or a polyhydric alcohol such as a glycol, preferably a water-miscible polyhydric alcohol, either alone or as a mixture with water and/or at least one of the monohydric alcohols mentioned.

Further additives which can be used for kneading and/or shaping are, inter alia, amines or amine derivatives such as tetraalkylammonium compounds or amino alcohols and carbonate-comprising compounds such as calcium carbonate. Such further additives are described, for instance, in EP 0 389 041 A1, EP 0 200 260 A1 or WO 95/19222.

The order of the additives such as template compound, binder, pasting agent, viscosity-increasing substance during shaping and kneading is in principle not critical.

In a further, preferred embodiment, the shaped body obtained by kneading and/or shaping is subjected to at least one drying step which is generally carried out at a temperature in the range from 25 to 500° C., preferably in the range from 50 to 500° C. and particularly preferably in the range from 100 to 350° C. It is likewise possible to carry out drying under reduced pressure or under a protective gas atmosphere or by spray drying.

In a particularly preferred embodiment, at least one of the compounds added as additives is at least partly removed from the shaped body during this drying process.

EXAMPLES

Comparative Example 1

Conventional Synthesis of MOF-5

96.7 g of $Zn(NO_3)_2 \cdot 4H_2O$ and 20.8 g of terephthalic acid are suspended in 2825 g of DEF (water content determined by the K. Fischer method: 0.02%). The reaction mixture (total water content determined by the K. Fischer method: 1%) is maintained at 130° C. for 3.5 hours. At the end of the reaction time, the water content of the reaction solution is 1.1%. After cooling, the solid is filtered off and washed with 4×500 ml of water-free acetone. The solid is firstly predried in a stream of nitrogen at room temperature for from 2 to 4 days and subsequently evacuated in a vacuum drying oven ($\leq 1$ mbar) for 16 hours.

Before determination of the surface area by means of $N_2$, the samples are in each case evacuated at 200° C. for a number of hours.

The following surface area values were found (Langmuir method):

| Sample | Surface area [m$^2$/g] |
| --- | --- |
| A (MH 148) | 2674 |
| B (MH 150) | 3016 |
| C (MH 155) | 2904 |
| D (MH 158) | 3530 |
| E (MH 159) | 2279 |
| F (MH 160) | 3684 |
| G (MH 161) | 2038 |
| H (MH 164) | 2811 |
| Average | 2867 ± 561 |

Example 2

Synthesis of MOF-5 with Removal of Water

The synthesis of example 1 is repeated, but this time vapors formed during the reaction are separated off by means of a slow stream of nitrogen via a distillation attachment. The mother liquor after filtration comprises only about 0.5% of H$_2$O. The further sample treatment is again carried out analogously to example 1.

The following surface area values are found (Langmuir method):

| Sample | Surface area [m$^2$/g] |
| --- | --- |
| I (MH 166) | 3372 |
| J (MH 167) | 3545 |
| K (MH 170) | 2940 |
| L (MH 183) | 3511 |
| M (MH 184) | 3628 |
| Average | 3399 ± 273 |

The results show that, owing to the removal of water from the reaction mixture, a framework having a higher specific surface area can be obtained and the standard deviation found on repeating the experiments is lower, which indicates better reproducibility.

Example 3

Synthesis of MOF-5 with Removal of Water

The synthesis of example 1 is repeated, but this time in the presence of 200 g of a freshly activated 3 Å molecular sieve. The mother liquor after filtration comprises only about 0.34% of H$_2$O. The further sample treatment is again carried out analogously to example 1. The sample has an N$_2$ surface area (Langmuir method) of 3182 m$^2$/g.

The invention claimed is:

1. A process for preparing a porous metal organic, if appropriate limited, framework, which comprises the step
    reaction of a reaction mixture in a liquid phase comprising at least one metal compound with at least one at least bidentate organic compound which can be coordinated to the metal, in the presence of a nonaqueous organic solvent in the presence of and/or with liberation of water, with the organic compound having at least two atoms selected independently from the group consisting of oxygen, sulfur and nitrogen via which the organic compound can coordinate to the metal, wherein water is withdrawn from the liquid phase of the reaction mixture during the reaction.

2. The process according to claim 1, wherein the water is at least water of crystallization of the metal compound or a constituent of the solvent or is formed by elimination in the reaction of the at least one metal compound with the at least one at least bidentate compound.

3. The process according to claim 1, wherein the at least one at least bidentate organic compound is derived from a dicarboxylic, tricarboxylic or tetracarboxylic acid or a sulfur analogue thereof.

4. A process for preparing a porous organoboron framework, which comprises the step
    reaction of a reaction mixture in a liquid phase comprising at least one compound having at least two boronic groups with at least one at least bifunctional organic compound which can be covalently bound to a boronic group, in the presence of a nonaqueous organic solvent, with the at least bifunctional organic compound having at least two atoms selected independently from the group consisting of oxygen, sulfur and nitrogen via which the bifunctional organic compound can be covalently bound to a boronic group, wherein water is withdrawn from the liquid phase of the reaction mixture during the reaction.

5. The process according to claim 1, wherein the water is withdrawn from the reaction mixture by distillation, by stripping or by means of adsorbents.

6. The process according to claim 1, wherein the reaction is carried out with stirring.

7. The process according to claim 1, wherein the reaction is carried out at a pressure of not more than 2 bar (absolute).

8. The process according to claim 1, wherein the reaction is carried out at a reaction temperature in the range from 80° C. to 180° C.

9. The process according to claim 1, wherein the nonaqueous organic solvent is a $C_{1-6}$-alkanol, DMSO, DMF, DEF, DMAc, acetonitrile, toluene, dioxane, benzene, chlorobenzene, MEK, pyridine, THF, ethyl acetate, optionally halogenated $C_{1-200}$-alkane, sulfolane, glycol, NMP, γ-butyrolactone, alicyclic alcohols, ketones, cycloketones, sulfolene or a mixture thereof.

10. The process according to claim 1, wherein one or more work-up steps which are carried out with exclusion of moisture follow.

* * * * *

UNITED STATES PATENT AND TRADEMARK OFFICE
CERTIFICATE OF CORRECTION

PATENT NO. : 7,847,115 B2
APPLICATION NO. : 12/161024
DATED : December 7, 2010
INVENTOR(S) : Markus Schubert et al.

It is certified that error appears in the above-identified patent and that said Letters Patent is hereby corrected as shown below:

On the title page, Item (30), the Foreign Application Priority Data has been omitted. Item (30) should read:

-- (30)   Foreign Application Priority Data

Feb. 10, 2006   (EP) ............................ 06101535.0 --

Signed and Sealed this
First Day of March, 2011

David J. Kappos
*Director of the United States Patent and Trademark Office*